United States Patent
Yao et al.

(10) Patent No.: US 6,972,344 B2
(45) Date of Patent: Dec. 6, 2005

(54) METHOD OF PRODUCING PURE 1,1-BIS-(4-HYDROXYPHENYL)-3,3,5-TRIMETHYLCYCLOHEXANE

(75) Inventors: Kazuhiko Yao, Wakayama (JP); Kenji Ekawa, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 11/013,822

(22) Filed: Dec. 16, 2004

(65) Prior Publication Data

US 2005/0165258 A1 Jul. 28, 2005

(30) Foreign Application Priority Data

Jan. 22, 2004 (JP) .............................. 2004-014188
Nov. 16, 2004 (JP) .............................. 2004-331416

(51) Int. Cl.[7] .......................................... C07C 39/17
(52) U.S. Cl. ..................................................... 568/721
(58) Field of Search ........................................ 568/721

(56) References Cited

U.S. PATENT DOCUMENTS

| | | | | |
|---|---|---|---|---|
| 4,982,014 A | * | 1/1991 | Freitag et al. | 568/721 |
| 5,336,812 A | * | 8/1994 | Salek et al. | 568/721 |
| 5,698,600 A | * | 12/1997 | Wulff et al. | 521/32 |
| 6,284,931 B1 | * | 9/2001 | Yao et al. | 568/721 |
| 6,673,973 B1 | * | 1/2004 | Yao et al. | 568/721 |
| 6,673,974 B1 | * | 1/2004 | Yao et al. | 568/721 |
| 6,673,975 B1 | * | 1/2004 | Yao et al. | 568/721 |

* cited by examiner

*Primary Examiner*—Michael L. Shippen
(74) *Attorney, Agent, or Firm*—Knobbe, Martens, Olson & Bear LLP

(57) ABSTRACT

A method of producing 1,1-bis-(4-hydroxyphenyl)-3,3,5-trimethylcyclohexane comprising: crystallizing a phenol adduct of 1,1-bis-(4-hydroxyphenyl)-3,3,5-trimethylcyclohexane from a solution comprising 1,1-bis-(4-hydroxyphenyl)-3,3,5-trimethylcyclohexane and phenol; washing the phenol adduct with a washing solution comprising phenol and water; decomposing by heating the washed phenol adduct in an aqueous solvent to remove phenol from the phenol adduct, thereby obtaining pure 1,1-bis-(4-hydroxyphenyl)-3,3,5-trimethylcyclohexane.

5 Claims, No Drawings

METHOD OF PRODUCING PURE 1,1-BIS-(4-HYDROXYPHENYL)-3,3,5-TRIMETHYLCYCLOHEXANE

BACKGROUND OF THE INVENTION

1. Field of the Invention

The present invention relates to a method of producing 1,1-bis(4-hydroxyphenyl)-3,3,5-trimethylcyclohexane (referred to as "BPTMC" hereinafter). More particularly, the invention relates to a method of producing high purity BPTMC by an acid condensation reaction of phenol with 3,3,5-trimethylcyclohexanone (referred to as "TMC" hereinafter), wherein a resultant solution comprising BPTMC and phenol obtained as a reaction product is isolated and purified by a simple procedure.

2. Description of the Related Art

In recent years, BPTMC has been used, for example, as raw materials for synthetic resins for the production of optical products such as optical disks, as well as for example as a raw material for polycarbonate resins for optical use. For these uses there is a strong need for producing colorless high purity BPTMC which is free of not only reaction byproducts but also of byproducts that are generated in the treatment for the purification of the reaction product, such as high boiling point byproducts and colored byproducts, residual phenol and trace impurities such as sodium, in a simple, highly selective, high yield procedure.

According to one known example of the method of producing BPTMC using TMC and phenol as raw materials, phenol is generally reacted with TMC in the presence of an acid catalyst, the resultant reaction mixture is neutralized after completion of the reaction, and an aqueous phase is removed, after which a phenol adduct with BPTMC is crystallized and isolated by cooling, the resulting adduct (adduct crystal) is dephenolized to obtain BPTMC. Conventionally, a steam distillation method and an evaporation method are generally used for removing phenol from this phenol adduct (dephenolization) as described in Japanese Patent Application Laid-open No. H02-088634, Published Japanese Translation of PCT Application No. H08-505644, and the like. However, a disadvantage of using these methods is that the resulting BPTMC is thermally deteriorated to cause coloration.

Also a method of producing colorless high purity BPTMC without impurities is disclosed in International Patent Publication No. WO 02/22533, in which the abovementioned phenol adduct is dissolved in a crystallizing solvent comprising an aromatic carbohydrate solvent and water, after which the crystals of BPTMC are crystallized (recrystallization), and then the resulting crystals are filtered.

SUMMARY OF THE INVENTION

As a result of studies on means to further simplify the process in the above-mentioned production method, the present inventors have found a method in which high purity BPTMC can be obtained without recrystallization and thus completed the invention.

According to the present invention, there is provided a method of producing 1,1-bis-( 4-hydroxyphenyl)-3,3,5-trimethylcyclohexane (BPTMC) in which a phenol adduct with BPTMC is crystallized from a solution comprising BPTMC and phenol, the resultant phenol adduct is isolated and then phenol is removed from said phenol adduct to obtain BPTMC, the method being characterized in that said phenol adduct is washed with a washing solution comprising phenol and water and then the phenol adduct thus washed is decomposed by heating in an aqueous solvent upon the isolation of said phenol adduct.

Further, according to the present invention, there is provided a method of producing BPTMC characterized in that the temperature of the solution comprising BPTMC and phenol is gradually lowered upon the crystallization of the phenol adduct with BPTMC (BPTMC-phenol adduct) from the solution in the abovementioned production method.

According to the method of producing BPTMC of the present invention, high purity BPTMC which is colorless and excellent in hue and has a low phenol content and further an extremely low content of metal impurities such as sodium and sulfur can be obtained in high yield without carrying out such a complicated operation as redissolution and recrystallization of the phenol adduct, upon the purification of the BPTMC-phenol adduct containing impurities such as byproducts and metals.

DETAILED DESCRIPTION OF THE PREFERRED EMBODIMENT

The present invention is a method of producing 1,1-bis-(4-hydroxyphenyl)-3,3,5-trimethylcyclohexane (BPTMC) in which a phenol adduct with BPTMC is crystallized from a solution comprising BPTMC and phenol, the resultant phenol adduct is isolated and then phenol is removed from said phenol adduct to obtain BPTMC, the method being characterized in that said phenol adduct is washed with a washing solution comprising phenol and water and then the phenol adduct thus washed is decomposed by heating in an aqueous solvent upon the isolation of said phenol adduct.

In the present invention, the solution comprising BPTMC and phenol can be any solution containing BPTMC and phenol and is not particularly limited, but preferably an oil phase containing BPTMC and phenol, which is obtained by reacting phenol and 3,3,5-trimethylcyclohexane in the presence of an acid catalyst, neutralizing the resulting reaction mixture after completion of the reaction and then removing a water phase; this water phase is cooled to crystallize the BPTMC-phenol adduct and the crystallized BPTMC-phenol adduct (phenol adduct crystal) is isolated, for example, by filtration to obtain the BPTMC-phenol adduct. In this case, the resulting phenol adduct crystal generally contains isomers, high boiling point byproducts such as polymers, colored byproducts and trace impurities such as sodium, besides BPTMC and phenol. Therefore, colorless high purity BPTMC could not generally be obtained without such operations as dissolution, recrystallization and filtration of this BPTMC-phenol adduct using a solvent.

However, the present inventors have found that high purity BPTMC can be obtained by washing this BPTMC-phenol adduct using a washing solution comprising phenol and water and then decomposing the washed phenol adduct by heating in an aqueous solvent. Presumably impurities in the abovementioned BPTMC-phenol adduct are mostly adhered onto the surface of the crystals and can be removed by washing with an aqueous phenol solution, so that the high purity BPTMC can be obtained simply by a thermal decomposing operation in an aqueous solution without such operations as redissolution and the like.

In the present invention, the phenol concentration of the aqueous phenol solution comprising phenol and water used for washing the BPTMC-phenol adduct is not particularly limited, but generally in the range of 5–90% by weight, preferably in the range of 8–80% by weight, more preferably in the range of 10–70% by weight. The amount of the aqueous phenol solution for washing is not particularly limited, but may generally be about 0.5 fold or more by weight of the BPTMC-phenol adduct. Further, the temperature of the aqueous phenol solution for washing ranges generally from room temperature to 80° C., preferably 30–70° C. The pressure for washing is not particularly limited, but is generally normal pressure.

The method of washing is not particularly limited, but the washing can be carried out, for example, by placing the BPTMC-phenol adduct and the aqueous phenol solution in a flask, stirring at about 60° C. for about 30 minutes and then filtrating for washing, or by placing the BPTMC-phenol adduct in a centrifugal dryer and spraying an aqueous phenol solution while spinning.

Next, the washed BPTMC-phenol adduct is decomposed by heating in an aqueous solvent. More specifically, the thermal decomposition in an aqueous solvent is carried out, for example, by placing the BPTMC-phenol adduct and water in a reaction vessel and heating under normal pressure or reduced pressure, thereby decomposing the adduct while distilling out generated phenol and water.

Further, according to the present invention, upon the crystallization of the BPTMC-phenol adduct from the solution comprising BPTMC and phenol in the above-mentioned production method, the high purity phenol adduct can be obtained as large crystals by gradually cooling said solution, which enables the production of colorless higher purity BPTMC by washing such BPTMC-phenol adduct using the abovementioned washing solution comprising phenol and water and then thermally decomposing the resulting washed BPTMC-phenol adduct in an aqueous solvent.

More specifically, for example, phenol and TMC are reacted in the presence of an acid catalyst, the reaction mixture obtained is neutralized after completion of the reaction, and then the water phase is removed, after which the resulting oil phase containing BPTMC and phenol is gradually cooled with a certain temperature gradient, preferably with 5–8° C./hour. In this way, crystals of BPTMC-phenol adduct having a large diameter with fewer impurities can be obtained.

The present invention will be explained by the following reference examples and examples; however, these examples are not construed to limit the scope of the invention.

REFERENCE EXAMPLE 1

Into a 1-L four necked flask equipped with a thermometer, a dropping funnel, a reflux condenser, and a stirrer were placed 188 g (2.0 moles) of phenol, 9.9 g of water, and 0.5 g of a 75% aqueous phosphoric acid solution, the temperature was adjusted to 20° C., and the air in the reaction system was replaced with nitrogen gas while stirring, after which hydrogen chloride gas was introduced. The gas component inside the reaction vessel was analyzed and the volumetric concentration of hydrogen chloride gas was adjusted to 80%.

While maintaining the temperature at 20° C., 21 g of a 15% aqueous solution of methyl mercaptan sodium salt was added dropwise, and then a mixture of 188 g (2.0 moles) of phenol and 70.0 g (0.5 mole) of 3,3,5-trimethylcyclohexanone was added dropwise over a period of 3 hours. After completion of the addition dropwise, the reaction was continued for another 3 hours while maintaining the temperature at 20° C. After completion of the reaction, the resulting reaction mixture was identified using liquid chromatography and NMR analysis, which showed that the product was the BPTMC of interest and the yield (molar quantity of BPTMC produced/molar quantity of material TMC) was 89.3% (as measured by liquid chromatography).

After completion of the reaction, the resulting reaction mixture was neutralized at pH 6.5 by adding an 18% aqueous sodium hydroxide solution while maintaining the temperature at 40–50° C. Next, the temperature of the reaction mixture thus neutralized was raised to 95° C. to dissolve the generated BPTMC adduct crystals, after which the resulting water phase was removed by separation, and the temperature of the oil phase obtained was gradually lowered to 40° C. with a temperature gradient of about 6° C./hour to crystallize the BPTMC-phenol adduct, and thus 177.9 g of crystals of the BPTMC-phenol adduct were obtained by centrifugal filtration. The result of liquid chromatography analysis showed that the adduct crystals thus obtained were consisted of 133.4 g of BPTMC, 44.2 g of phenol and 0.3 g of remaining and had an APHA color value of 90 (10% methanol solution, as measured by the JIS method). Further, the trace impurities were 170 ppm sodium (as measured by atomic adsorption spectrometry) and 300 ppm sulfur (as measured by inductively coupled plasma atomic emission spectrometry).

Further, the analytical values in the following examples and comparative examples are all measured in the same manner as described in Comparative Example 1 above.

EXAMPLE 1

Into a centrifugal dryer (Sanyo Rikagaku Kikai Seisakusho) equipped with a 10-cm diameter basket and a 200-mesh filter cloth was placed 30 g of the crystals of BPTMC-phenol adduct obtained in Reference Example 1, and then 60 g of a 10% phenol aqueous solution (a mixture of 10% by weight phenol and 90% by weight water) at 30° C. was sprinkled onto the phenol adduct crystals over a period of about 1–2 minutes at a rotating speed of 4000 rpm at normal temperature and under normal pressure.

Then the rotating speed was raised to 4000 rpm or more to separate the solid portion from the liquid.

Next, 28 g of the washed adduct and 84 g of water were placed into a four necked flask equipped with a thermometer, a stirrer, and a distillation device to distil out phenol and water by heating under normal pressure. The resultant water-phenol mixture was cooled and then filtered by centrifugation, and the resultant filtrate was dried under reduced pressure to obtain 21.4 g of the purified BPTMC product of interest.

The yield was 95% based on the phenol adduct crystals, and the product had an APHA color value of 40, a phenol content of 210 ppm (measured by liquid chromatography analysis; the phenol content was measured in the same manner in the following Examples and Comparative Examples), a BPTMC purity of 99.9% (measured by high performance liquid chromatography analysis; the purity was measured in the same manner in the following Examples and Comparative Examples), a metal impurity (sodium) level of less than 5 ppm and a sulfur content of less than 1 ppm.

EXAMPLE 2

A purified BPTMC product (20 g) was obtained in the same manner as described in Example 1, except that a 70% phenol aqueous solution was used in place of the 10% phenol aqueous solution used in Example 1. The yield was 88% based on the phenol adduct crystals, and the product had an APHA color value of 20, a phenol content of 300 ppm, a BPTMC purity of 99.9%, a metal impurity (sodium) level of less than 5 ppm and a sulfur content of less than 1 ppm.

EXAMPLE 3

A purified BPTMC product (19 g) was obtained in the same manner as described in Example 2, except that the 70% phenol aqueous solution used in Example 2 was heated to 60° C. for use in washing.

The yield was 84% based on the phenol adduct crystals, and the product had an APHA color value of 10, a phenol content of 150 ppm, a BPTMC purity of 99.9%, a metal impurity (sodium) level of less than 5 ppm and a sulfur content of less than 1 ppm.

COMPARATIVE EXAMPLE 1

The reaction was carried out as described in Reference Example 1 and the reaction mixture obtained after completion of the reaction was neutralized at pH 6.5 by adding an 18% aqueous sodium hydroxide solution while maintaining the temperature at 40–50° C. Next, the temperature of the reaction mixture thus neutralized was raised to 95° C. to dissolve the generated BPTMC adduct crystals, after which the resulting water phase was removed by separation, and the temperature of the oil phase obtained was rapidly lowered to 40° C. with a temperature gradient of about 20° C./hour to crystallize the BPTMC-phenol adduct, and the crystals of the BPTMC-phenol adduct were obtained by centrifugal filtration.

The resulting phenol adduct crystals had an APHA color value of 120.

Next, 30 g of the adduct crystals thus obtained and 90 g of water were placed into a four necked flask equipped with a thermometer, a stirrer, and a distillation device to distil out phenol and water by heating under normal pressure. Then this water mixture was cooled and then filtered by centrifugation, and the resultant filtrate was dried under reduced pressure to obtain 20.2 g of the purified BPTMC product of interest.

The product had an APHA color value of 130, a phenol content of 340 ppm, and a BPTMC purity of 99.7% and thus could not be a high purity product.

COMPARATIVE EXAMPLE 2

The adduct crystals (30 g) used in Example 1 were washed with 180 g of water heated to 90° C. The resultant crystals were dried under reduced pressure to obtain a purified BPTMC product.

The product had an APHA color value of 80, a phenol content of 1900 ppm, and a BPTMC purity of 99.5% and thus could not be a high purity product.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of producing 1,1-bis-(4-hydroxyphenyl)-3,3,5-trimethylcyclohexane comprising:
    crystallizing a phenol adduct of 1,1-bis-(4-hydroxyphenyl)-3,3,5-trimethylcyclohexane from a solution comprising 1,1-bis-(4-hydroxyphenyl)-3,3,5-trimethylcyclohexane and phenol;
    washing said phenol adduct with a washing solution comprising phenol and water;
    decomposing by heating the washed phenol adduct in an aqueous solvent to remove phenol from the phenol adduct, thereby obtaining pure 1,1-bis-(4-hydroxyphenyl)-3,3,5-trimethylcyclohexane.

2. The method according to claim 1, wherein in the crystallizing step, the temperature of said solution comprising 1,1-bis-(4-hydroxyphenyl)-3,3,5-trimethylcyclohexane and phenol is gradually lowered.

3. The method according to claim 1, wherein a phenol concentration of the washing solution comprising phenol and water is in the range of 5–90% by weight.

4. The method according to claim 1, wherein the temperature of the washing solution is in the range of 30–70° C.

5. The method according to claim 2, wherein said solution comprising 1,1-bis-(4-hydroxyphenyl)-3,3,5-trimethylcyclohexane and phenol is gradually cooled with 5–8° C./hour.

* * * * *